United States Patent [19]

Ohkuma et al.

[11] Patent Number: 5,523,395
[45] Date of Patent: Jun. 4, 1996

[54] LECTIN SPECIES OBTAINED FROM JAPANESE HORSESHOE CRABS AND FROM SOUTHERN HORSESHOE CRABS

[75] Inventors: Seiichi Ohkuma; Khomei Yanagi, both of Tokyo; Kuniharu Wada, Fukushima; Isami Tsuboi, Ibaraki; Shoji Kimura, Ibaraki; Masahito Matsukawa, Ibaraki; Nobuyuki Sato, Ibaraki, all of Japan

[73] Assignee: Maruha Corporation, Tokyo, Japan

[21] Appl. No.: 277,939

[22] Filed: Jul. 20, 1994

Related U.S. Application Data

[63] Continuation of Ser. No. 934,140, Aug. 21, 1992, abandoned.

[30] Foreign Application Priority Data

| Sep. 2, 1991 | [JP] | Japan | 3-246463 |
| Sep. 30, 1991 | [JP] | Japan | 3-280813 |

[51] Int. Cl.$^6$ .................................................. C07K 3/00
[52] U.S. Cl. ........................... 530/396; 530/857; 424/538
[58] Field of Search ............................ 424/538; 530/396, 530/857

[56] References Cited

U.S. PATENT DOCUMENTS

| 4,457,865 | 7/1984 | Miller | 530/396 |
| 4,520,111 | 5/1985 | Miller | 530/396 |
| 5,330,897 | 7/1994 | Pindak et al. | 435/7.23 |

FOREIGN PATENT DOCUMENTS

| 53-092800 | 8/1978 | Japan . |
| 84045679 | 11/1984 | Japan . |
| 04338400 | 11/1992 | Japan . |
| 8804303 | 6/1988 | WIPO | 530/396 |

OTHER PUBLICATIONS

Bishayee et al., 1980, Biochimica et Biophysica Acta 623:89–97.
Corfield and Schauer, Cell Biology Monographs, "B. The Occurrence of Sialic Acids", 10:6–50.
Doral et al., 1981, Archives of Biochemistry and Biophysics 209:325–333.
Dorai et al., 1982, Federation of European Biochemical Socities 148:98–102.
Goldstein et al., in The Lectins, Properties, Functions and Applications in Biology and Medicine eds. I. E. Liener et al. Ch 2 pp. 35–244, Academic Press 1986.
Hakomori, 1984, Am. Rev. Immunol 2:103–126.
Laemmli, 1970, Nature 227:680–685.
Lennarz, W. J., The Biochemistry of Glycoproteins and Proteoglycans, 3:142–47.
Mandal et al., 1989, Biochem. J. 257:65–71.
Mandal et al., 1990, Experlentla 46:433–441.
Marchalonis et al., 1968, J. Mol. Biol. 32:453–465.
Mohan et al., 1982, Biochem. J. 203:253–261.
Murayama et al., 1981, J. Biochem. 89:1593–1598.
Nowak et al., 1975, Biochimica et Biophysica Acta 393:115–123.
Ohyama et al., 1991, Biomedical and Biophysical Research Communications 178:79–84.
Oppenhelm et al., 1974, Biochemical and Biophysical Research Communications 58:1127–1135.
Roche et al., 1974, Biochimica et Biophysica Acta 371:242–254.
Roche et al. 1975, Febs Letters 57:245–249.
Reutter et al., "Cell Biology Monographs," J. Biological Significance of Sialic Acids, 10:264–305.
Shimizu et al., 1979, Biomedical Applications of the Horseshoe Crab (Limulidae), 625–639.
Shishikura et al., 1983, J. Biochem. 93:1539–1546.
Ravindranath, M. H. et al., "American Zoologist," vol. 24(3), 1984, p. 55A, #301.
White, M. K. et al. Abstracts of the Annual Meeting, 1989, p. 97, #D–89.
Mureson, U et al., "The J. of H istechem and Cyteo Chem.," vol. 30 (9), 1982, pp. 938–946.
Kaplan, R., et al., "Molecular Characterization of Limulin, a Sialic Acid Binding Lactin . . . *Polyphemus*," Biochemistry 16(19), 1977 pp. 4297–4303.
Shimizu, S., et al., "Lectins in the Hemdymth of Japanese Horseshoe Crab, *Tachypleus Trilantatus*," Biochimica et Biophysica Acta 500, 1977, pp. 71–79.
Hall, J. L., et al. "Heterogeneity of Lobster Applications I. Purification . . . Characterization," Biochem. 13(4), 1977, pp. 821–827.
Dorai, D. T., et al., "Fractionation of sialoglycoproteins on an Immobilized . . . Lectin," Anal. Biochem. 115, 1981, pp. 130–137.

*Primary Examiner*—Marian C. Knode
*Assistant Examiner*—Kristin Larson
*Attorney, Agent, or Firm*—Pennie & Edmonds

[57] ABSTRACT

Disclosed are two lectin species isolated from the hemolymph of Japanese horseshoe crabs and Southern horseshoe crabs which bind to N-acetylneuraminic acid and N-glycolylneuraminic acid, but not to N-acetylglucosamine, glucoronic acid, or N-acetylgalactosamine.

2 Claims, 3 Drawing Sheets

LECTIN SPECIES OBTAINED FROM JAPANESE HORSESHOE CRABS AND FROM SOUTHERN HORSESHOE CRABS

This is a continuation of application Ser. No. 07/934,140, filed Aug. 21, 1992, now abandoned.

FIELD OF THE INVENTION

The present invention relates to novel lectins obtained from the hemolymph, respectively, of an American horseshoe crab (*Limulus polyphemus*), of a Japanese horseshoe crab (*Tachypleus tridentatus*) and a Southern horseshoe crab (*Tachypleus gigas*). The lectins are useful as reagents for detecting sialic acids such as N-acetylneuraminic acid and N-glycolylneuraminic acid and their complex sugars.

BACKGROUND OF THE INVENTION

Currently, three genera and four species are known in horseshoe crabs. Of these horseshoe crabs, lectin, an erythrocyte aggregation factor, is isolated and purified from three species, an American horseshoe crab (*Limulus polyphemus*), a Japanese horseshoe crab (*Tachypleus tridentatus*), and an Indian horseshoe crab (*Carcinoscrpius rotunda cauda*). The lectins obtained from these horseshoe crabs have poor specificity to sialic acids. In addition, it is reported that the lectins also recognize other sugars [Marchalonis, J. J. & Edelman, G. M., 1968: J. Mol. Biol. 32: 453–465; Annie-Claude Roche and Michel Monsigny, 1974: Biochemica et Biophysica Acta. 371: 242–254; T. P. Nowak and S. H. Barondes, 1975: Biochemica et Biophysica Acta. 393: 115–123; Shimizu, S., Ito, M., & Niwa, M., 1977, Biochem. Biophys. Acta 393: 115–123; Shimizu, S., Ito, M., Takahashi, N., & Niwa, M., 1979," Biomedical Applications of the Horseshoe Crab (Limulidae) pp. 625–639, Cohen, E., ed., Alan R. Liss, Inc., New York; F. Shishikura and K. Sekiguchi., 1983, 93:1539–1546; S. Bishayee and D. Thambi Dorai., 1983, Biochemica et Biophysica Acta. 623: 89–97].

SUMMARY OF THE INVENTION

Three lectins of the present invention are novel and useful as reagents for detecting sialic acids such as N-acetylneuraminic acid and N-glycolylneuraminic acid complex sugars having bound-type sialic acids. Many complex sugars containing bound-type sialic acids are known as physiologically active substances. The lectins of the present invention are useful to isolate or purify the physiologically active substances, or are used as a carrier adsorbent of affinity chromatography.

DETAILED DESCRIPTION OF THE INVENTION

It is an object of the present invention to provide isolated, purified lectins that specifically recognize sialic acids and their sugars and apparently differ in properties from known lectins. The lectins of the present invention can be isolated and purified by a combination of affinity chromatography using sialoglycoprotein ligands and gel filtration. Three isolated, purified lectins have the following property, that is, binding to sugars:

N-acetylamino sugar −

N-acetylneuraminic acid +

N-glycolylneuraminic acid +

In contrast, known lectins isolated from the hemolymph of an American horseshoe crab and a Japanese horseshoe crab can also bind to N-acetylamino sugar, and known lectins isolated from the hemolymph of an Indian horseshoe crab can also bind to glucuronic acid. The lectins of the invention apparently differ in the binding properties to sugars from lectins known in the art. Therefore, these lectins are novel.

The present invention will be further described by Examples.

EXAMPLE I

Glycophorin HA was prepared from equine erythrocyte membranes by the method of Murayama (1981: J. Biochem, 89: 1593–1598).

A 25 ml sample of AFFIGEL-10 was suspended in 25 ml of dimethyl formamide containing 25 mg of glycophorin HA and incubated for 30 min at 25 °C. The suspension was mixed with 25 ml of 0.5M Tris-HCl buffer (pH7.2) and incubated for 24 hr at 25° C. with gentle shaking. The resultant glycophorin HA-AFFIGEL-10 was then washed with 50 mM Tris-HCl/pH 7.2 containing 0.5M KSCN and 0.3M NaCl and equilibrated with 50 mM Tris-HCl/pH 7.2 containing 10 mM $CaCl_2$ and 0.3M NaCl. A 30 ml hemolymph sample was applied to a glycophorin HA-AFFIGEL-10 column (3.0×8.0) previously equilibrated with 50 mM Tris-HCl/pH7.2 containing 0.3M NaCl and 10 mM $CaCl_2$ (Buffer A). The column was washed with the same buffer and absorbed matters were eluted with 50 mM Tris-HCl/pH7.2 containing 0.3M NaCl (Buffer B). The fractions showing both absorbance at 280 nm and hemagglutinating activity against the equine erythrocytes were subsequently pooled and concentrated with an ultrafiltration membrane (pM-10). The concentrated samples were applied to a SEPHACRYL S-300 column (1.0×70 cm). Proteins were eluted with Buffer B. The fractions showing both absorbance at 280 nm and hemagglutinating activity against the equine erythrocytes were pooled.

The results suggest that although the three lectin species of the present invention differ in physical and chemical properties from each other, the lectins of the present invention differ in specificity to sialic acids and their complex sugars from the known lectins of an American horseshoe crab, a Japanese horseshoe crab, and an Indian horseshoe crab.

EXAMPLE 2

Figure 1:
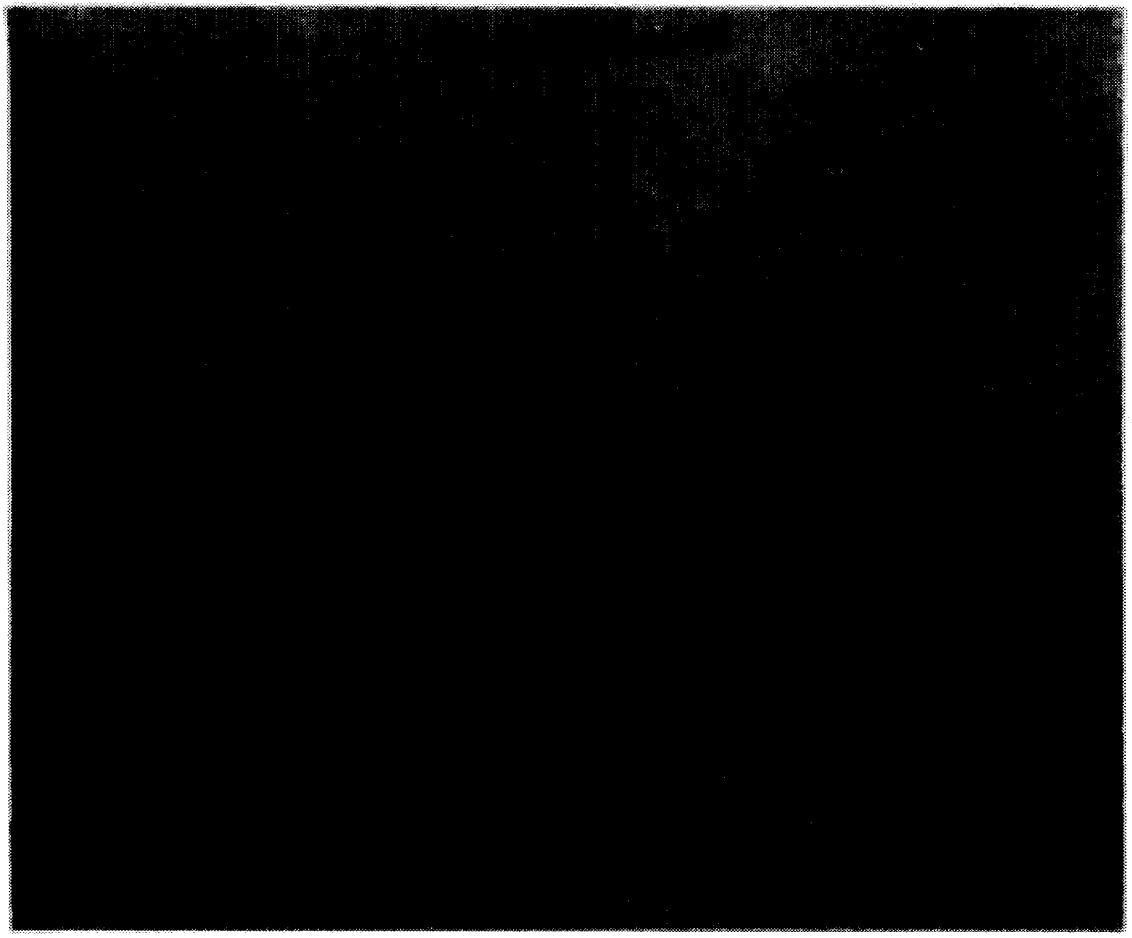
FIG. 1 shows the results of electrophoresis of three lectins using a polyacrylamide gel (Disk-PAGE). Lane 1 represents the lectin obtained from *L. polyphemus*; Lane 2, from *T. tridentatus*; Lane 3, from *T. gigas*.
Figure 2:
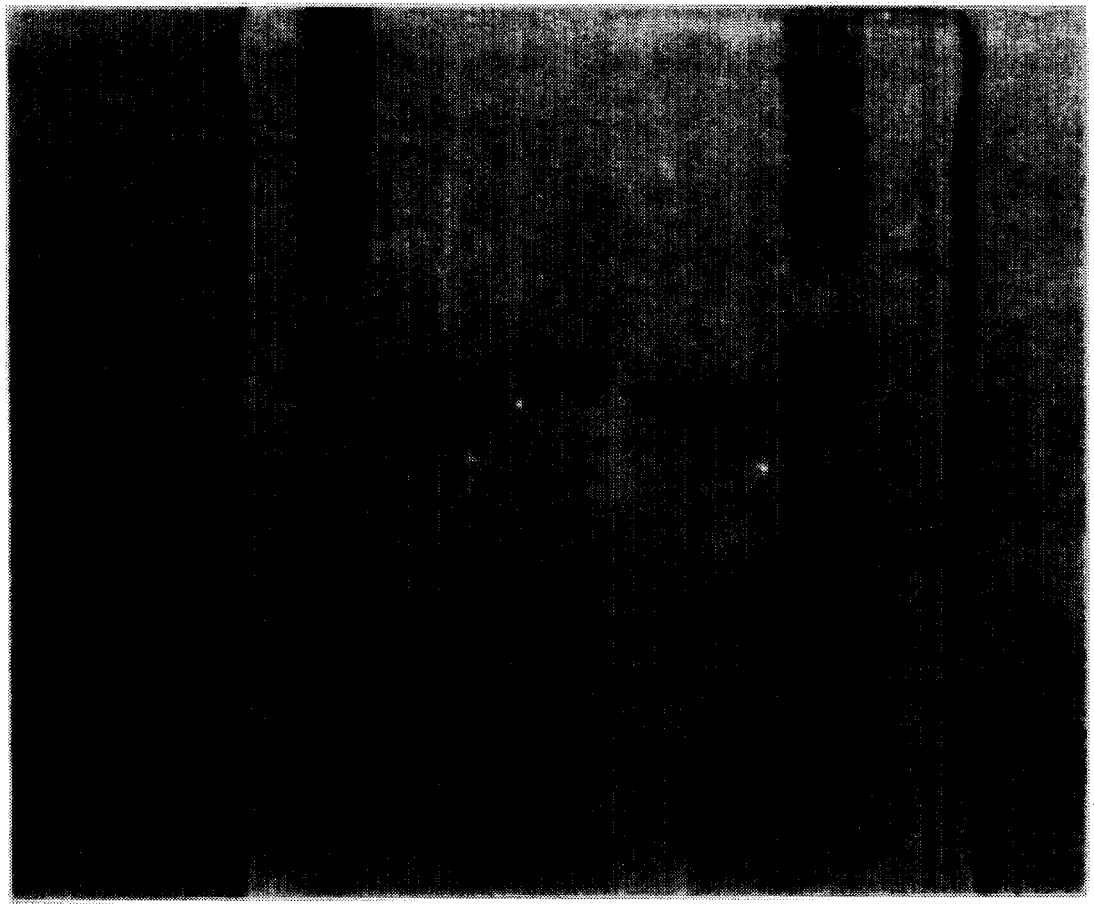
FIG. 2 shows the results of electrophoresis of the three lectins using a denaturing polyacrylamide gel (SDS-PAGE). M represents molecular weight markers; Lane 1 represents the lectin obtained from *L. polyphemus*; Lane 2, from *T. tridentatus*; Lane 3, from *T. gigas*.

Lectins isolated and purified from an American horseshoe crab, a Japanese horseshoe crab, and a Southern horseshoe crab are electrophoresed through a polyacrylamide gel (Disk-PAGE) and SDS-PAGE (see FIGS. 1 and 2). Although lectins obtained from the horseshoe crabs described above have a different relative mobility, they are a single band on Disk-PAGE (FIG. 1). On SDS-PAGE, lectins obtained from an American horseshoe crab and a Southern horseshoe crab are a single band and have a molecular weight of 30 kd while lectin obtained from a Japanese horseshoe crab is two bands and has a molecular weight of 31 kd and 32 kd (Table 1).

TABLE 1

|  | Molecular weight (SDS-PAGE) |
|---|---|
| L. polyphemus lectin | 30,000 Da |
| T. tridentatus lectin | 31,000 Da and 32,000 Da |
| T. gigas lectin | 30,000 Da |

EXAMPLE 3

Figure 3:
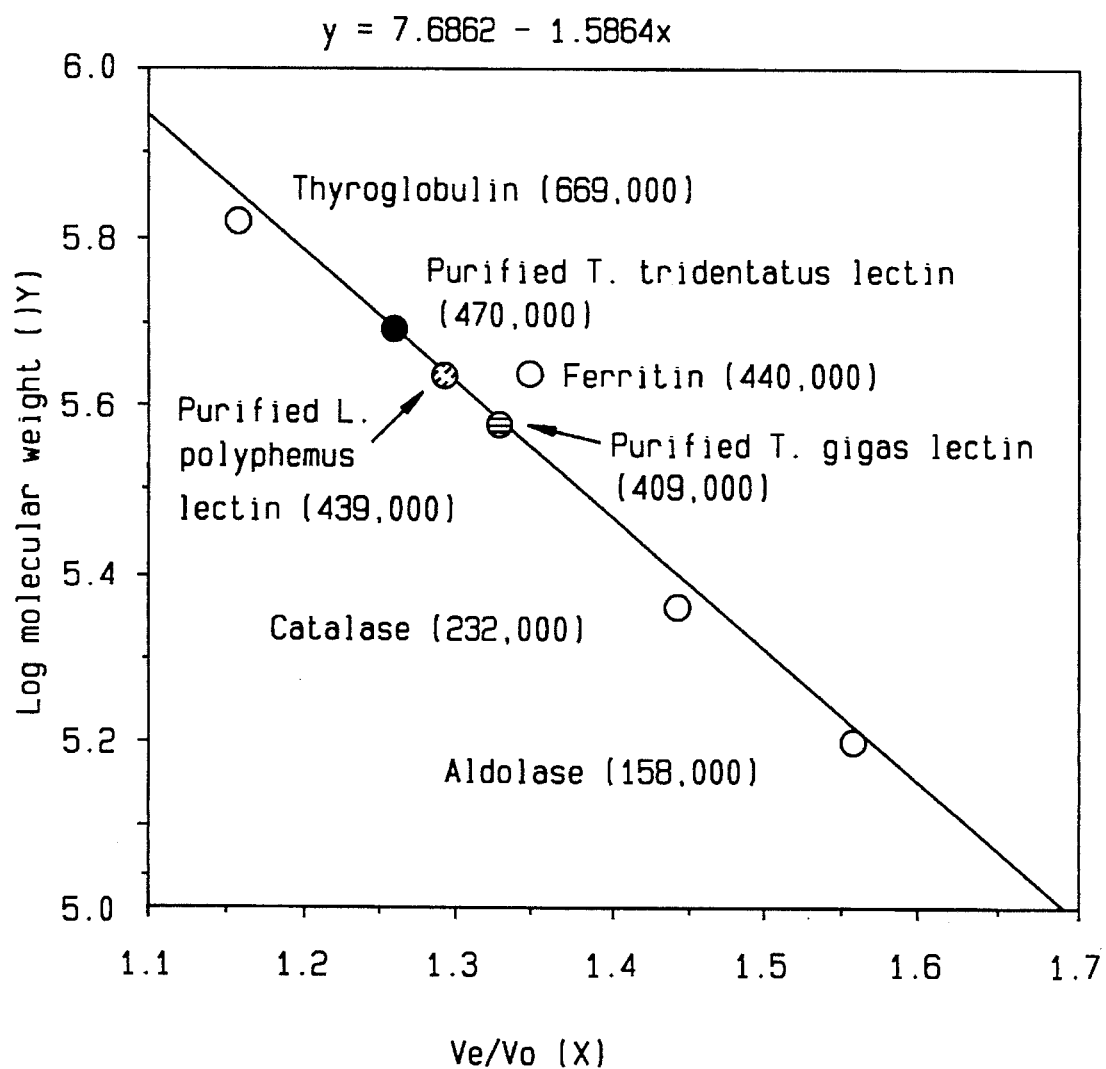
FIG. 3 shows the results of the measurement of the molecular weight of the lectins determined using gel filtration using SEPHACRYL S-300.

Molecular weights of the lectins obtained from the hemolymph of an American horseshoe crab, a Japanese horseshoe crab, and a Southern horseshoe crab were determined by gel filtration method using Sephacryl-S300. The molecular weight (daltons) of the lectin is 470,000 (American horseshoe crab), 439,000 (Japanese horseshoe crab) and 409,000 (Southern horseshoe crab) (see FIG. 3).

EXAMPLE 4

As presented in Table 2, none of neutral sugars, glucosamine, N-acetylhexosamines, glucuronic acid, and asialoglycoproteins and ovomucoid inhibited the hemagglutination of equine erythrocytes with three sialic acid-specific lectins even at a concentration as high as 10,000 μg/ml. On the contrary, the hemagglutination of equine erythrocytes with three sialic acid-specific lectins were inhibited, by glycophorin HA, glycophorin A, bovine submaxillary mucin, fetuin, N-acetylneuraminic acid and N-glycolylneuraminic acid in that order.

TABLE 2

| Materal | L. polyphemus lectin | T. tridentatus lectin | T. gigas lectin |
|---|---|---|---|
| Glucose | n.i | n.i | n.i |
| Mannose | n.i | n.i | n.i |
| Galactose | n.i | n.i | n.i |
| Mannose | n.i | n.i | n.i |
| Fucose | n.i | n.i | n.i |
| Mannose | n.i | n.i | n.i |
| Galactose | n.i | n.i | n.i |
| Glucuronic acid | n.i | n.i | n.i |
| Glucosamine | n.i | n.i | n.i |
| Galactosamine | n.i | n.i | n.i |
| N-Acetylglucosamine | n.i | n.i | n.i |
| N-Acetylgalactosamine | n.i | n.i | n.i |
| N-Acetylneuraminic acid | 5,000 | 5,000 | 5,000 |
| N-Glycolylneuraminic acid | 5,000 | 5,000 | 5,000 |
| Glycophorin HA | 0.488 | 0.488 | 0.061 |
| Glycophorin A | 1.953 | 1.953 | 0.488 |
| Bovine submaxillary mucin | 3.906 | 15.62 | 7.812 |
| Ovomucoid | n.i | n.i | n.i |
| Fetuin | 15.62 | 15.62 | 0.977 |
| NeuAcα2-3Galβ1-4Glu | 50,000 | 50,000 | 50,000 |
| NeuAcα2-6Galβ1-4Glu | 12,500 | 12,500 | 12,500 |
| Asialoglycophorin HA | n.i | n.i | n.i |
| Asialoglycophorin A | n.i | n.i | n.i |

TABLE 2-continued

| Materal | L. polyphemus lectin | T. tridentatus lectin | T. gigas lectin |
|---|---|---|---|
| Asialofetuin | n.i | n.i | n.i | n.i., No inhibition of agglutination at 10,000 μ/ml

EXAMPLE 5

Any one of the lectins of the present invention has such a property that the lectin strongly aggregates equine erythrocytes rather than human erythrocytes (Table 3).

TABLE 3

|  | Human erythrocytes | | Horse erythrocytes | |
|---|---|---|---|---|
|  | +Ca | −Ca | +Ca | −Ca |
| L. polyphemus lectin | 4 | − | 128 | − |
| T. tridentatus lectin | 16 | − | 256 | − |
| T. gigas lectin | 32 | − | 512 | − |

(−)Not agglutinate

EXAMPLE 6

Any one of the lectin of the present invention requires $Ca^{2+}$ ion for the aggregation reaction of equine erythrocytes. However, the minimum requirment of $Ca^{2+}$ ions differs from one lectins to another (Table 4).

TABLE 4

|  | Require quantity of $CaCl_2$ (mM) |
|---|---|
| L. polyphemus lectin | 5.00 mM |
| T. tridentatus lectin | 1.25 mM |
| T. gigas lectin | 0.10 mM |

The results suggest that although the three lectin species of the present invention differ in physical and chemical properties from each other, the lectins of the present invention differ in specificity to sialic acids and their complex sugars from the known lectins of an American horseshoe crab, a Japanese horseshoe crab, and an Indian horseshoe crab.

What is claimed is:

1. An isolated lectin obtained from the hemolymph of Japanese horseshoe crabs, Tachypleus tridentatus, which has two bands with a molecular weight of 31,000 and 32,000 daltons by SDS-PAGE and specifically binds to N-acetylneuraminic acid and N-glycolylneuraminic acid but not to N-acetylglucosamine, glucuronic acid or N-acetylgalactosamine.

2. An isolated lectin obtained from the hemolymph of Southern horseshoe crabs, Tachypleus gigas, which has a molecular weight of 30,000 daltons by SDS-PAGE and specifically binds to N-acetylneuraminic acid and N-glycolylneuraminic acid but not to N-acetylglucosamine, glucuronic acid or N-acetylgalactosamine.

* * * * *